United States Patent
Perea Rodriguez et al.

(10) Patent No.: US 7,374,767 B2
(45) Date of Patent: May 20, 2008

(54) PEPTIDES FOR THE TREATMENT OF CANCER ASSOCIATED WITH THE HUMAN PAPILLOMA VIRUS (HPV) AND OTHER EPITHELIAL TUMORS

(75) Inventors: Silvio Ernesto Perea Rodriguez, Playa (CU); Osvaldo Reyes Acosta, Playa (CU); Nelson Francisco Santiago Vispo, Playa (CU); Yaquelin Puchades Izaguirre, Juanelo (CU); Ricardo Silva Rodriguez, Playa (CU); Alejandro Moro Soria, Zoológico (CU); Alicia Santos Savio, Playa (CU); Luis Javier González López, Playa (CU); Belkis González Barrios, Playa (CU)

(73) Assignee: Centro de Ingenieria Genetica y Biotechologia, Playa, Ciudad de La Habana (CU)

( * ) Notice: Subject to any disclaimer, the term of this patent is extended or adjusted under 35 U.S.C. 154(b) by 219 days.

(21) Appl. No.: 10/499,458

(22) PCT Filed: Dec. 4, 2002

(86) PCT No.: PCT/CU02/00010

§ 371 (c)(1),
(2), (4) Date: Feb. 22, 2005

(87) PCT Pub. No.: WO03/054002

PCT Pub. Date: Jul. 3, 2003

(65) Prior Publication Data

US 2006/0233742 A1    Oct. 19, 2006

(30) Foreign Application Priority Data

Dec. 20, 2001   (CU) ..................................... 0309/01

(51) Int. Cl.
*A61K 39/12*   (2006.01)

(52) U.S. Cl. .................. 424/204.1; 435/69.1; 530/300
(58) Field of Classification Search ............. 424/204.1; 435/69.1; 530/300
See application file for complete search history.

(56) References Cited

U.S. PATENT DOCUMENTS

2001/0029022 A1   10/2001   Fisher et al.

FOREIGN PATENT DOCUMENTS

| EP | 0 412 762 | 2/1991 |
|---|---|---|
| EP | 0 531 080 | 3/1993 |
| EP | 0 666 270 | 8/1995 |
| JP | 0 969 013 | 1/2000 |
| WO | 95 01374 | 1/1995 |
| WO | WO 01/64835 | * 9/2001 |

* cited by examiner

*Primary Examiner*—Ali R. Salimi
(74) *Attorney, Agent, or Firm*—Hoffmann & Baron, LLP

(57) ABSTRACT

This invention is related to the Molecular Pharmacology field and especially to the development of peptides useful for treating epithelial tumors and mainly those associated to oncogenic types of HPVs. The main objective of this invention is to identify peptides whose structure permits to block the Casein Kinase II (CKII) phosphorylation domain by direct interaction with such a site. In the present invention it is shown eleven cyclic peptides with different aminoacid sequences which inhibit the CKII phosphorylation in vitro, exhibit cytotoxicity on HPV-16 transformed cells (CaSki) and also increase the sensitivity of these cells to the cytostatic effect of interferon (IFN). Furthermore, the invention relates to the use of these peptides conjugated or fused to other peptides and chemical compounds which penetrates into cells as well as with the use of both peptide and chemical mimetic molecules.

30 Claims, 7 Drawing Sheets

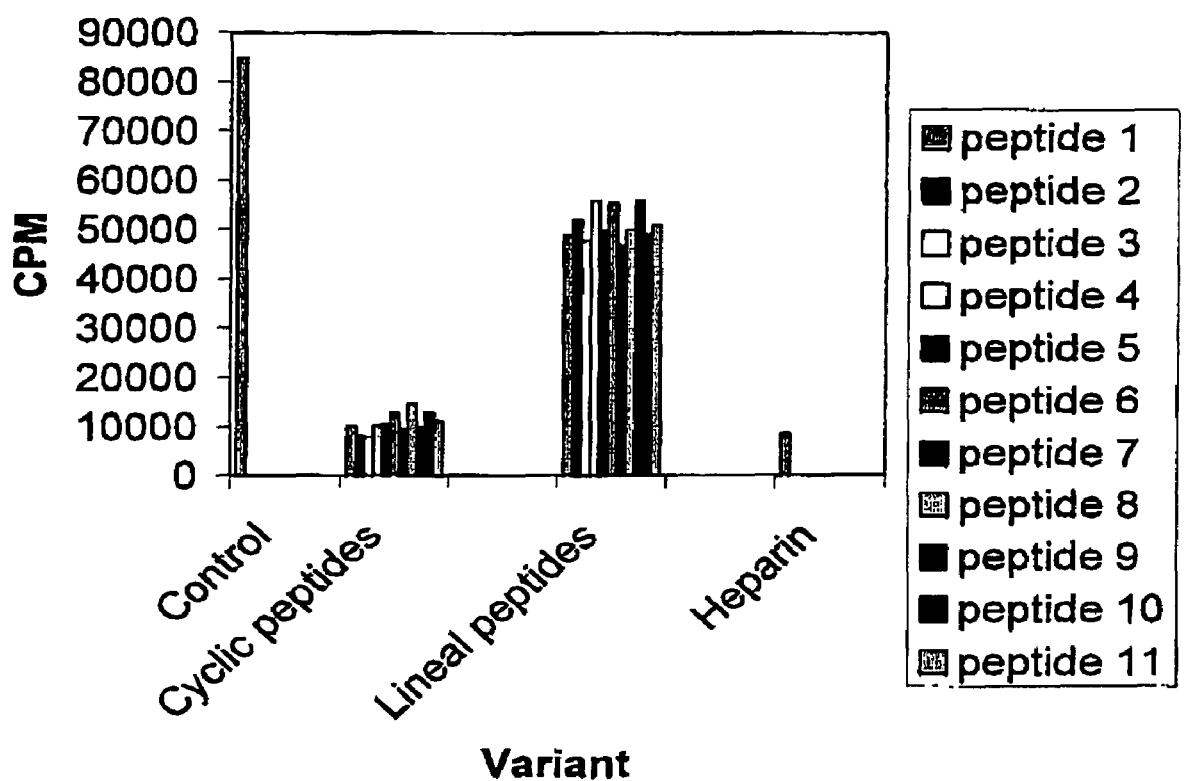
Figur 2

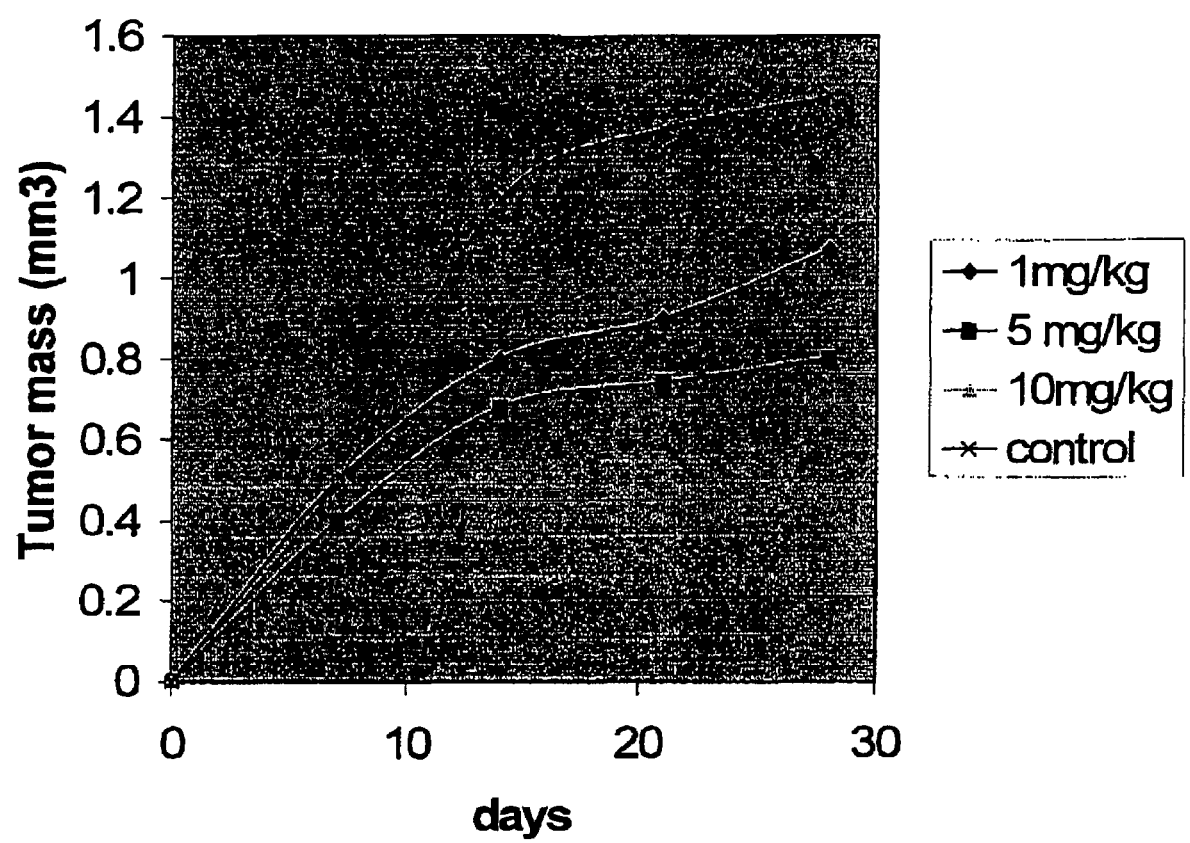

PEPTIDES FOR THE TREATMENT OF CANCER ASSOCIATED WITH THE HUMAN PAPILLOMA VIRUS (HPV) AND OTHER EPITHELIAL TUMORS

This application is the U.S. National Phase of International Application Number PCT/CU02/00010 filed on 4 Dec. 2002, which is incorporated herein by reference.

BACKGROUND OF THE INVENTION

This invention is related to the Molecular Pharmacology field and especially to the development of peptides useful for treating HPV-associated epithelial tumors as it permits the blocking of the Casein Kinase II (CKII) phosphorylation domain by direct interaction with such a site.

The CKII is a threonine/Serine enzyme involved in the cellular proliferation and its intracellular localization is mainly into nucleus during malignant transformation process (Tawfic S, Yu S, Wang H, Faust R, Davis A, Ahmed K, 2001, Histol. Histopathol. 16:573-582).

Based on the findings reporting CKII high levels in different epithelial solid tumors, it has been assumed that phosphorylation elicited by this enzyme is an important event in malignant transformation and a tumor progression marker (Seldin D C, Leder P, 1995, Science 267:894-897) (Faust R A, Gapany M, Tristani P, Davis A, Adams G L, Ahmed K, 1996, Cancer Letters 101:31-35). On the other hand, the CKII over expression in transgenic mice leads to the tumorigenesis in the mammary glands by increasing the Wnt/beta-catenine signal transduction pathways on these mammary epithelial cells (Landesman-Bollag E, Romien-Mourez R, Song D H, Sonenshein G E, Cardiff R D, Seldin D C, 2001, Oncogene 20:3247-3257).

Among epithelial tumors, those originated by HPVs represent a great fraction. For instant, most of the genitourinary tumors are associated to these oncoviruses and the presence of HPV DNA sequences has been demonstrated in 99.7% of the tumors coming from squamous cervical cells (Walboormers J M, Jacobs M V, Manos M M, Bosch F X, Kummer J A, Shah K V, Snijders P J, Peto J, Meijer C J, Muñoz N, 1999, J. Pathol 189:12-19). Likewise, the WHO has reported about 500 000 cervical cancer patients annually worldwide (Parkin D M, Laara E, Muir C S, 1980, Int. J. Cancer 41:184-1972). In Cuba, 370 women with cervical cancer die annually due to this disease (Organizacion Panamericana de la Salud,1999, Basic Country Health Profiles for the Americas. Cuba, 206-219)

HPVs are classified in oncogenic and not oncogenic according to whether the lesions progress toward malignancy or not (Lorincz A T, Temple G F, Kurman R J, Jenson A B, Lancaster W D, 1987, J. Natl. Cancer Inst. 79:671-677). HPV-16 and -18 are associated to intraepitelial neoplasia that generally progress toward malignancy and also both HPV types are associated to more than 90% of the displasias and cervical carcinomas (Fujinaga Y, Shimada M, Okasawa K, Fukushima M, Kato I, Fujinaga K, 1991 J. Gen. Virol 72:1039-1044).

As no therapeutic or prophylactic vaccine is still available for eradication of HPV-associated tumors, the employment of inhibitors targeting viral transcription and viral oncoproteins, become more attractive. Biomodulators like IFNs have been used with some efficacy in certain HPV-associated diseases like condyloma, plantar warts, and respiratory papillomatosis (Koromilas A E, Li S, Matlashewski G, 2001. Cytokine & Growth Factor Reviews 12:157-170). In previous experiments on HPV-transformed cells (HeLa), we have demonstrated that continuous exposition with IFN alpha produces a reversion of the malignant phenotype of these cells with the concomitant inhibition of the HPV mRNA expression (López-Ocejo O, Perea S E, Reyes A, Vigoa L, López-Saura P, 1993. J. IFN Res 13:369-375). In the same cellular model, we found that IFN alpha modulates the HPV mRNA through the repression of endogenous viral transcription (Perea S E, López-Ocejo O, Garcia-Milian R, Araña M J, 1995, J. IFN & Cytokine Res 15;495-501). In agreement with the results obtained in cell lines, we observed that IFN alpha treatment modulated the mRNA expression in a pilot study in cervical cancer patients (Garcia-Milian R, Rios M A, Diaz D, Silveira M, Guilar O, AmigóM, Arafla M J, Perea S E, 1996, J. IFN and Cytokine Res 16:709-713). In spite of the promissory findings about the use of IFN as regulator of the HPV mRNA expression, mounting data indicate a variable IFN response and the resistance phenomenon toward this cytokine has been reported between the 40 and 50% of the patients during clinical trials (Arany I, Tyring S K, Stanley M A, Tomai M A, Miller R L, Smith M H, McDermott, D J, Slade H B, 1999, Antiviral Res 43:55-63). Some molecular and clinical evidences indicate that E7 oncoprotein plays a central role on the IFN-resistance phenomenon. For example, it has been reported that E7 binds to the IFN-induced transcription factor (p48) thus affecting the IFN response by blocking the transcriptional activation (Barnard P and McMillan N A J, 1999, Virology 259:305-313). Furthermore, the alteration of the IFN regulatory factor (IRF-1) in the presence of E7 has been also reported (Park J S, Kim E J, Kwon H J, Hwang E S, Namkoong S E, Um S J, 2000, J Biol Chem 275:6764-6769) (Perea S E, Massimi P, Banks L, 2000, J Mol Med 5:661-666). In clinical trials, the IFN response has been regarded to be depending on the E7 expression in the HPV-containing lesions (Frazer I H, McMillan N A J, 1997, Papillomatosis and condyloma acuminate. Clinical Applications of the Interferons (R Stuart Harris and R D Penny, eds) Pp 79-90. Chapman and Hall Medical, London). The E7 oncoprotein plays an essential role on the malignant transformation elicited by these oncogenic viruses. Thus, it has been demonstrated that E7-induced immortalization of primary cells leads to mutations and chromosomal aberrations since the beginning of the immortalization process (Mougin C, Humbey O, Gay C, Riethmuller D, 2000, J. Gynecol Obstet. Biol. Reprod 29:13-20). On the other hand, we have demonstrated that stable transfection with the E7 gene leads to the development of a IFN-resistant phenotype on sensitive tumor cells (Moro A, Calixto A, Suárez E, Araña M J, Perea S E, 1998, Bioch Bioph Res Comm 245:752-756). Likewise, it has been reported that E7 oncoprotein binds and blocks the function of tumor suppressor genes like the Retinoblastoma (Rb) and the Insulin-like Growth Factor Binding Protein-3" (IGFBP-3) through the Cys 24 and the C-terminal domain respectively (Nevins J R, 1992, Science 258:424-429) (Zwerschke W and Jansen-Durr P. 2000, Advances in Cancer Res 78:1-29). Similarly, the Ser 31/Ser 32 doublets in E7 protein have shown to be substrate for the CKII enzyme (Hashida T. Yasumoto S, 1990, Biochem. Biophys. Res. Comm 172:958-964) and this domain is essential for both the transformant capacity of this oncoprotein (Barbosa M S, Edmonds C, Fisher C, Schiller J T, Lowy D R, Vousden K, 1990, EMBO J 9:153-160) (Chi n W-M, Parker J N, Schmidt-Grimminger D-C, Broker T R, Chow L T, 2000, Cell Growth & Differentiation 11:425-435) and the inhibition of the IFN signaling cascade (Perea S E, López-Ocejo O, Garcia Millán R, Banks L, Araña M J, 1996, Eur. Cytokine Net 7:503).

Based on the role of the CKII phosphorylation site in the HPV-resistance to IFN and cancer development, the designing of drugs blocking such a domain could become as useful tools for cancer therapy. Molecules inhibiting the CKII phosphorylation site either on E7 or in other cell substrates have not been described so far.

Concerning the E7 oncoprotein, only peptides blocking the Rb binding site (Cys 24) (Webster K R, Koleman K G, 1997, U.S. Pat. No. 5,625,031)(Oliff A I, Riemen M W, EP 0412762 A2 910213) and other C-terminal regions (39-98) have been described (Pidder J-D, Zwerschke W, 2000, EP0969013).

Some vaccine candidates focused to develop HPV E7-specific CTL response have been so far described in clinical or pre-clinical trials (Chen C, Wang C C, Hung C, Pardoll D M, Wu T, 2000, Vaccine 18:2015-2022) (Chen CH, Ji H, Suh K W, Choti M A, Pardoll D M, Wu T C, 1999, Gene Ther 12:1972-1981). However, the approaches focused to the CTL response face different obstacles related to the HPV biology. For instant, HPV oncogenic types down-regulate the MHC class I antigens which are essential for the CTL response (Connor M E, Stern P L, 1990, Int J Cancer 46:1029-1034). Furthermore, E7 expression has been associated with local immunosupression at the tumor environment and this could also affect the appropriated development of the CTL response (Le Buanec H, D'Anna R, Lachgar A, Zagury J F, Bernard J, Ittlele D, d'Alessio P, Hallez S, Giannouli C, Burny A, Bizzini B, Gallo R C, Zagury D, 1999, Biomed Pharmacother 53:424-431) (Lee S J, Cho Y S, Shim J H, Lee K A, Ko K K, Choe Y K, Park S N, Hoshino T, Kim S, Dinarello C A, Yoon D Y, 2001, J Immunol 167:497-504). According to the above elements, it seems that combining CTL vaccines and pharmaceuticals targeting E7, could be of great perspectives.

Likewise, the approach of preventive HPV-vaccines faces a high benefit and cost risk due to different biological and social aspects including: 1) Long latency period after the HPV primary infection, 2) poor understanding of the HPV infection mechanism, 3) no animal model for the appropriated HPV propagation, 4) specie specificity and 5) the evaluation of the social impact of a preventive HPV vaccine could take quite long. Therefore, the using of pharmaceuticals specifically targeting viral oncoproteins could provide advantages over those approaches focused to the manipulation of the immune system.

ESSENCE OF THE INVENTION

The essence and novelty of this invention lies on the description for the first time of cyclic peptides allowing the direct inhibition of the CKII phosphorylation site as well as the cytotoxicity produced in vivo on HPV-16 cervical carcinoma cells. Furthermore, these peptides increase the sensitivity of the cells to the cytostatic effect of IFN.

DETAILED DESCRIPTION OF THE INVENTION

The invention is mainly referred to peptides able to bind the CKII phosphorylation site which exhibits the following sequences:

| (a) | CSVRQGPVQKC | (SEQ. ID. NO. 1) |
| (b) | CSSCQNSPALC | (SEQ. ID. NO. 2) |
| (c) | CQIPQRTATRC | (SEQ. ID. NO. 3) |
| (d) | CAKQRTDPGYC | (SEQ. ID. NO. 4) |
| (e) | CWMSPRHLGTC | (SEQ. ID. NO. 5) |
| (f) | CRNCTVIQFSC | (SEQ. ID. NO. 6) |
| (g) | CHYIAGTVQGC | (SEQ. ID. NO. 7) |
| (h) | CPLVSLRDHSC | (SEQ. ID. NO. 8) |
| (i) | CKQSYLHHLLC | (SEQ. ID. NO. 9) |
| (j) | CFQPLTPLCRC | (SEQ. ID. NO. 10) |
| (k) | CQSYHELLLQC | (SEQ. ID. NO. 11) |

The invention also includes any homologue variant or mimetic from the peptides mentioned, that has been obtained by synthesis or recombinant way, as well as any fusion peptide containing the peptides described in the list. Any peptide, whose structure permits to block the CKII phosphorylation site in their respective substrates, is assumed as homologue variant. Likewise, any chemical molecule (no peptidic) whose structure permits to block such a phosphorylation site, is assumed as a mimetic variant.

Other object of the invention is the pharmaceutical composition which comprises one or more of the peptides described in the invention as well as an appropriated carrier.

Likewise, the invention comprises the use of the mentioned peptides alone or combined with any other appropriated molecule as cytokines and interferons to: 1) inhibit the proliferation of tumor cells, 2) treating both HPV-associated and not associated cancer and 3) treating HPV-associated lesions at the pre-malignant stages.

Furthermore, the peptides of the invention could be employed for treating HPV-infected patients resistant toward interferon treatment.

In other respect of the invention, it comprises one expression vector for mammalian cells containing a DNA sequence which codes for any of the peptides above referred.

The peptides of the invention have a cyclic structure and they are mainly characterized by the ability to bind the CKII phosphorylation site and abrogate such biochemical event. The peptides are described on the list enclosed. On the other hand, the in vivo effects produced by the peptides on HPV-16 transformed cells are also shown.

The peptides described were defined by their ability of both inhibiting the phosphorylation of the sequence RRREEETEEE (SEQ. ID. NO. 12) previously reported as the optimal consensus domain for the CKII phosphorylation (Promega Cat: V5661) and the phosphorylation site contained in the region 28-38 of the HPV-16 E7 oncoprotein.

To define the peptides described in the invention, one 11-aminoacid cyclic peptide library was constructed and expressed on the P8 region from filamentous phages. The screening of the library was performed using the synthetic 28-38 region of E7 as target, which was also conjugated to biotin for fixing it to a solid surface. Selection of those phages bound to the 28-38 region of E7 was carried out by immunodetection using an specific antibody against the P8 region in the phage. Finally, DNA corresponding to the eleven phages with high capacity of binding to the 28-38 region of E7, was sequenced and the respective peptides were chemically synthesized by the solid phase method. The synthetic peptides were further purified by HPLC, analyzed by mass spectrometry and finally evaluated respecting the in vitro and in vivo efficacy.

According to this invention, in spite of the different aminoacid sequences among the cyclic peptides described here, they equally inhibit the CKII phosphorylation event. This fact denotes that the interaction of these peptides with the CKII phosphorylation site is mainly based on their structure rather than the sequence itself.

In this invention, it is also demonstrated that lineal peptides exhibit a lower capacity of inhibiting the CKII phosphorylation site. This finding reinforces the importance of structure in the binding capacity of these peptides to such a domain. Also, this finding suggests the efficacy of other mimetic molecules, which bind to the CKII phosphorylation site.

In order to achieve the intracellular action on the CKII endogenous substrates, the described peptides can be chemically conjugated or genetically fused to the cell penetrating peptides belonging to proteins like the Human Immunodeficiency Virus (HIV-1) Tat 1(Schwarze SR, Dowdy SF, 2000,. Trends Pharmacol 21:45-48), the transcription factor coded by the Drosophyla Antenapedia gene (Derossi D, et al, 1996, J. Biol Chem 271:18188-18193), the Herpes Simplex Virus (HSV) VP22 protein (Lindgreen M, et al., 2000, Trends Pharmacol Sci 21:99-103), the penetratin and transportan (Gariepy J, Kawamura K, 2001, Trends Biotech 19:21-28) among others. To test the in vivo hypothesis in this invention, the cyclic peptides were synthesized fused to the cell penetrating peptide reported for the HIV-1 Tat I protein (GRKKRRQRRRPPQC (SEQ ID NO: 13)) and one nuclear localization signal belonging to the SV 40 T large antigen (KKKRKVE (SEQ ID NO: 14)).

Data shown in this invention clearly indicate that cyclic peptides exhibit cytotoxicity in a dose-dependent manner on cervical carcinoma cells transformed by HPV-16 (CaSki). These results suggest the employment of these peptides as a therapeutical tool for treating tumors from the same hystologic origin as well as from premalignant stages like the cervical intraepithelial neoplasia. Likewise, the in vivo experimental data showed that cyclic peptides were more effective than their respective lineal form thus reinforcing the importance of structure on the effect itself.

Likewise, the cyclic peptides described in this invention are effective on Hela cells containing the HPV-18 as well as on H-82 cells derived from Non-Small Lung cell cancer negative for HPV. These results correlate to those obtained in vitro in this invention where peptides block nor only the CKII phosphorylation site on the HPV-16 E7 but also they block it in other proteins containing such a site. The fact that the peptides described here are effective on HPV-negative tumor cells provides an argument for its potential employment in other epithelial tumors. Other results in this invention indicate that treatment of CaSKi cells with the cyclic peptides described here increases the cell sensitivity to the cytostatic effect of IFN alpha. Considering previous evidences showing that the CKII phosphorylation site on the HPV-16 E7 is required for blocking the IFN signaling cascade (Perea S E, López-Ocejo O, Garcia Millán R, Banks L, Araña M J, 1996, Eur. Cytokine Net 7:503), the peptides described here can be useful in bypassing the common IFN-resistance observed on HPV infection.

The object of this invention can be also related to the DNA coding for each peptide described here. This DNA could be introduced in a mammalian expression vector and further transfected into both HPV-16-transformed and -no transformed cells. The vector containing the oligonucleotide that codes for each peptide can be also used as an alternative for the gene therapy in HPV-associated cancer.

In principle, the peptides described here can be used in HPV-associated diseases along with other agents as well as with therapeutic vaccines based cellular response against HPV.

This invention is illustrated by the following examples:

EXAMPLE 1:

Effect of the peptides on the CKII phosphorvlation site:

This assay is based on an in vitro phosphorylation reaction using the substrate sequence RRREEETEEE (SEQ ID NO: 12) which represents the optimized consensus domain for the CKII phosphorylation. The reaction is performed in 50 µl of Tris:HCL 25 mM pH 7.5, 1 µCi$^{32}$P-γATP, 100 µM ATP, 2 mg/ml of the substrate peptide, 0.2 M NaCl, 10 mM MgCl and 1 unit of the CKII enzyme (Promega). Reaction is incubated at 37° C. during 10 minutes.

Afterward, 5 µl of reaction were spotted onto PE-81 chromatography paper (Whatmann) and four washes with 10 mM H3PO$_4$ were made. Finally, the radioactivity associated to the filters was measured and the cpm levels show the CKII enzymatic activity in each sample. Simultaneously, an specific CKII inhibitor like heparin is included in the assay as an internal control. Data show in the FIG. 1 demonstrated that cyclic peptides inhibit the CKII phosphorylation by 80%. Also, lineal peptides inhibit the CKII phosphorylation of the 28-38 region on E7 although to a lesser extent compared with cyclic form. These evidences indicate that the peptides described here inhibit the CKII phosphorylation site and suggest that structure plays an essential role on their interaction with the target sequences.

EXAMPLE 2

Effect of the Peptides on the HPV-16 E7 Phosphorylation

This assay is based on the in vitro phosphorylation reaction of the HPV-16 E7 oncoprotein expressed in *E. Coli* as a fusion protein to the Glutathione *S Transferase* (GST). Before enzymatic reaction, the E7-GST fusion protein was purified by affinity chromatography using Glutathione Sepharose beads (Pharmacia). The mixture reaction is performed in 50 µl de buffer Tris:HCL 25 mM pH 7.5, 1 µCi de $^{32}$P-γATP, 100 µM ATP, 40 µl of the beads containing E7-GST, 0.2 M NaCl, 10 mM MgCl and 1 unit of CKII (Promega). The reaction is incubated at 37° C. during 40 min. Afterward, the beads are washed away three times with 0.5 ml of the buffer and finally the phosphorylation level of the E7-GST is analyzed by 10% SDS-PAGE electrophoresis. The visualization of the phosphorylated proteins was performed by developing X-Rays films previously exposed to the dried gels. The quantification of the E7 phosphorylation was made by densitom try. Data in FIG. 2 indicate that the peptides described here are equally effective in terms of the inhibition of the CKII phosphorylation site on the HPV-16 E7.

EXAMPLE 3

Effect of the Peptides on the Proliferation of HPV-16 and HPV-18-Transformed Cells (CaSki and HeLa Respectively In this assay, CaSki or HeLa cells were seeded at $2 \times 10^4$ cells/ml in 96-well plates (Costar) using DMEM supplied with 10% of Fetal Calf Serum (FCS) (Gibco). After 24 hours, peptides were added to the culture medium at doses comprising a range between 15 µM and 500 µM. The incubation was performed during 96 hours in 5%$CO_2$ and finally 20 µl of a MTS solution (1.90 mg/ml) Promega were added to each well. Plates were subsequently maintained one hour at the same incubation conditions and the absorbance at 490 nm was finally analyzed. Results are expressed as percent of growth respect the control without peptides. For this purpose, both cyclic and lineal peptides were chemically synthesized fused to the HIV-1 Tat-1 cell penetrating peptide which is able to penetrate into cytoplasm and nucleus (Schwarze S R, Dowdy S F, 2000, Trends Pharmacol 21:45-48). Data obtained from this experiment demonstrated that peptides described here produce a dose-dependent effect both on CaSki (HPV-16) and HeLa (HPV-18) cells (FIGS. 3 A and 3 B). This example shows that peptides from this invention are effective nor only for HPV-16 but also for HPV-18.

EXAMPLE 4

Effect of the Peptides on the Proliferation of HPV-Negative Tumor Cells

In this assay, H-82 cells (Small Lung Cells Cancer) were seeded at $2 \times 10^4$ cells/ml in 96-well plates (Costar) using DMEM supplied with 10% of Fetal Calf Serum (FCS) (Gibco). After 24 hours, peptides were added to the culture medium at doses comprising a range between 15 µM and 500 µM. The incubation was performed during 96 hours in 5%$CO_2$ and finally 20 µl of a MTS solution (1.90 mg/ml) Promega were added to each well. Plates were subsequently maintained one hour at the same incubation conditions and the absorbance at 490 nm was finally analyzed. Results are expressed as percent of growth respect the control without peptides. For this assay, the cyclic peptides described in the invention fused to the HIV-1 Tat-1 cell penetrating peptide were employed as referred above. Results obtained from this experiments demonstrated that peptides from this invention produce a dose-dependent effect on the cell proliferation of H-82 cells. In FIG. 4 it is demonstrated that peptides from the invention are effective not only for HPV-transformed cells but also for tumor cells from other localization and histological types like Small Lung Cell Cancer.

EXAMPLE 5

Effect of the Peptides on the HPV-16 Response Toward IFN Treatment in CaSki Cells In this assay, CaSki cells were seeded at $2 \times 10^4$ cells/ml in 96-well plates (Costar) using DMEM supplemented with 10% FCS (Gibco). After 24 hours, 120 µM of each peptide were added to the culture medium. Twenty four hours later, alpha IFN was added in range between 1000 and 31.5 U/ml. The incubation was performed during 96 hours in 5% $CO_2$ and 20 µl of MTS 1.90 mg/ml were added afterward. Furthermore, plates were maintained one hour at the same conditions and the absorbance at 490 nm was finally read. Data are shown as percent of growth respect to the control. In these experiments, the peptides described in the invention were used in their cyclic variant fused to the cell penetrating peptide belonging the HIV Tat-1 protein as mentioned above. Results observed in the FIG. 5 demonstrate that previous incubation of CaSki cells with the peptides described in the invention makes these cells sensitive to the antiproliferative effect of alpha IFN. These data suggest the utility of the peptides described in the invention for treating HPV-infected patients who are refractory to the IFN therapy.

EXAMPLE 6

Antitumor Effect of the CKII Phosphorylation Inhibitory Peptide in Human Tumors Implanted in Nude Mice Models For these experiments, 6-8 week old female BalbC nude mice were used. The tumor implantation was performed using H-125 cells (Non-Small Lung Cell Cancer) that were resuspended in saline solution (PBS) at 1000 000 cells/ml. Cell suspension was inoculated subcutaneously in the abdomen. Peptide administration (sequence 1 on the list) was made together with the cells and continued every other day until completing one month of treatment. In this assay, doses ranging between 1 and 10 mg/Kg of weight were evaluated. To examine the antitumor effect, parameters progression. These data show the antitumor efficacy of the CKII phosphorylation inhibitory peptide in a model of human tumor implanted in experimental animals.

Advantages of the Invention

1. Provides pharmaceuticals of wide application spectrum which are nor only useful in HPV-associated diseases but also in solid tumors with high levels of CKII endogenous activity.

2. The fact that the 28-38 region is conserved among HPVs, it provides the possibility of using this pharmaceutical in diseases associated to different HPV types.

3. Peptides as therapeutical molecules exhibit low antigenicity when administered to human beings.

4. Is a pharmaceutical of easy manufacturing and low cost.

BRIEF DESCRIPTION OF FIGURES

FIG. 2: Effect of peptides on the HPVE7 CKII phosphorylation

FIG. 3 B: Effect of peptides on the proliferation of HeLa cells

FIG. 6: Antitumor effect of the CKII phosphorylation inhibitory peptide in human tumors implanted in nude mice

The invention claimed is:

1. A peptide comprising an amino acid sequence as set forth in:

a). CSVRQGPVQKC; (SEQ ID NO: 1)
b). CSSCQNSPALC; (SEQ ID NO: 2)
c). CQIPQRTATRC; (SEQ ID NO: 3)
d). CAKQRTDPGYC; (SEQ ID NO: 4)
e). CWMSPRHLGTC; (SEQ ID NO: 5)
f). CRNCTVIQFSC; (SEQ ID NO: 6)
g). CHYIAGTVQGC; (SEQ ID NO: 7)
h). CPLVSLRDHSC; (SEQ ID NO: 8)
i). CKQSYLHHLLC; (SEQ ID NO: 9)
j). CFQPLTPLCRC; or (SEQ ID NO: 10)
k). CQSYHELLLQC; (SEQ ID NO: 11)

wherein the peptide binds and inhibits a Casein Kinase II (CKII) phosphorylation site.

2. A peptide according to claim 1, wherein the peptide has a cyclic structure.

3. A peptide according to claim 2, wherein the peptide is contained in a fusion polypeptide.

4. A peptide according to claim 1, wherein the peptide is contained in a fusion polypeptide.

5. A pharmaceutical composition comprising
a). a peptide selected from the group consisting of
  i). CSVRQGPVQKC (SEQ ID NO: 1);
  ii). CSSCQNSPALC (SEQ ID NO: 2);
  iii). CQIPQRTATRC (SEQ ID NO: 3);
  iv). CAKQRTDPGYC (SEQ ID NO: 4);
  v). CWMSPRHLGTC (SEQ ID NO: 5);
  vi). CRNCTVIQFSC (SEQ ID NO: 6);
  vii). CHYIAGTVQGC (SEQ ID NO: 7);
  viii). CPLVSLRDHSC (SEQ ID NO: 8);
  ix). CKQSYLHHLLC (SEQ ID NO: 9);
  x). CFQPLTPLCRC (SEQ ID NO: 10);
  xi). CQSYHELLLQC (SEQ ID NO: 11);

and
b). a pharmaceutically-acceptable carrier.

6. A pharmaceutical composition according to claim 5, further comprising a cytokine.

7. A pharmaceutical composition according to claim 6, wherein the cytokine is interferon (IFN).

8. A pharmaceutical composition according to claim 5, wherein the peptide has a cyclic structure.

9. A pharmaceutical composition according to claim 8, further comprising a cytokine.

10. A pharmaceutical composition according to claim 9, wherein the cytokine is interferon (IFN).

11. A method for inhibiting tumor cell proliferation, comprising administering to a mammal an effective amount of a peptide comprising an amino acid sequence as set forth in:
a). CSVRQGPVQKC (SEQ ID NO: 1);
b). CSSCQNSPALC (SEQ ID NO: 2);
c). CQIPQRTATRC (SEQ ID NO: 3);
d). CAKQRTDPGYC (SEQ ID NO: 4);
e). CWMSPRHLGTC (SEQ ID NO: 5);
f). CRNCTVIQFSC (SEQ ID NO: 6);
g). CHYIAGTVQGC (SEQ ID NO: 7);
h). CPLVSLRDHSC (SEQ ID NO: 8);
i). CKQSYLHHLLC (SEQ ID NO: 9);
j). CFQPLTPLCRC (SEQ ID NO: 10); or
k). CQSYHELLLQC (SEQ ID NO: 11),
wherein the peptide binds and inhibits a Casein Kinase II (CKII) phosphorylation site.

12. A method according to claim 11, wherein the tumor is a human papillomavirus (HPV)-associated tumor.

13. A method according to claim 11, wherein the tumor is a premalignant human papillomavirus (HPV)-associated tumor.

14. A method according to claim 11, further comprising administering a cytokine.

15. A method according to claim 14, wherein the cytokine is interferon (IFN).

16. A method according to claim 11, wherein the mammal is infected with human papillomavirus (HPV) and is resistant toward treatment with interferon (IFN).

17. A method according to claim 11, wherein the peptide has a cyclic structure.

18. A method according to claim 17, wherein the tumor is a human papillomavirus (HPV)-associated tumor.

19. A method according to claim 17, wherein the tumor is a premalignant human papillomavirus (HPV)-associated tumor.

20. A method according to claim 17, further comprising administering a cytokine.

21. A method according to claim 20, wherein the cytokine is interferon (IFN).

22. A method according to claim 17, wherein the mammal is infected with human papillomavirus (HPV) and is resistant toward treatment with interferon (IFN).

23. A method according to claim 11, wherein the peptide is contained in a fusion polypeptide.

24. A method according to claim 23, wherein the tumor is a human papillomavirus (HPV)-associated tumor.

25. A method according to claim 23, further comprising administering a cytokine.

26. A method according to claim 25, wherein the cytokine is interferon (IFN).

27. A method according to claim 23, wherein the mammal is infected with human papillomavirus (HPV) and is resistant toward treatment with interferon (IFN).

28. A mammalian expression vector comprising a nucleotide sequence that encodes a peptide comprising an amino acid sequence as set forth in:
   a). CSVRQGPVQKC (SEQ ID NO: 1);
   b). CSSCQNSPALC (SEQ ID NO: 2);
   c). CQIPQRTATRC (SEQ ID NO: 3);
   d). CAKQRTDPGYC (SEQ ID NO: 4);
   e). CWMSPRHLGTC (SEQ ID NO: 5);
   f). CRNCTVIQFSC (SEQ ID NO: 6);
   g). CHYIAGTVQGC (SEQ ID NO: 7);
   h). CPLVSLRDHSC (SEQ ID NO: 8);
   i). CKQSYLHHLLC (SEQ ID NO: 9);
   j). CFQPLTPLCRC (SEQ ID NO: 10); or
   k). CQSYHELLLQC (SEQ ID NO: 11).

29. A mammalian expression vector according to claim 28, wherein the peptide has a cyclic nature.

30. A mammalian expression vector according to claim 28, wherein the peptide is contained in a fusion polypeptide.

* * * * *

UNITED STATES PATENT AND TRADEMARK OFFICE
CERTIFICATE OF CORRECTION

| | | |
|---|---|---|
| PATENT NO. | : 7,374,767 B2 | Page 1 of 1 |
| APPLICATION NO. | : 10/499458 | |
| DATED | : May 20, 2008 | |
| INVENTOR(S) | : Perea Rodriguez et al. | |

It is certified that error appears in the above-identified patent and that said Letters Patent is hereby corrected as shown below:

IN THE PATENT:

Column 2, line 13:

Now reads:    "Arafla M J"

Should read:    --Araña M J--

Signed and Sealed this

Twenty-third Day of September, 2008

JON W. DUDAS
*Director of the United States Patent and Trademark Office*

SEQUENCE LISTING

<160> NUMBER OF SEQ ID NOS: 14

Figure 1:
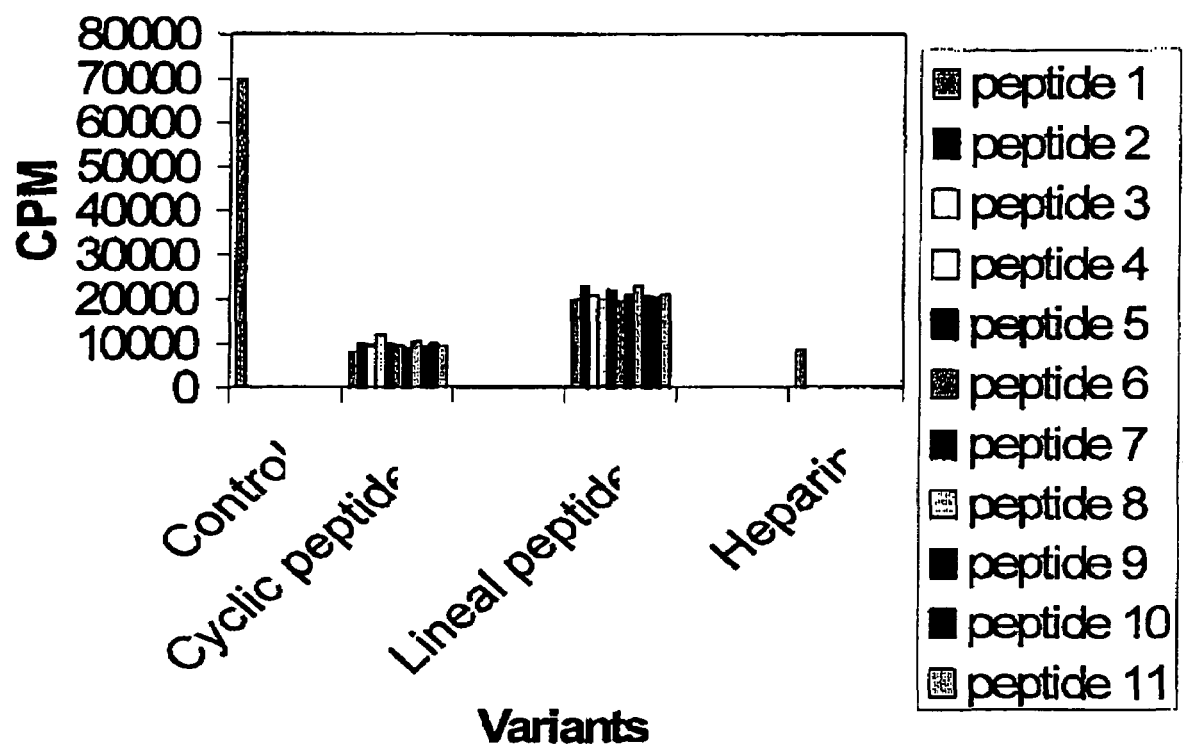
FIG. 1: Effect of peptides on the CKII phosphorylation
Figure 3A:
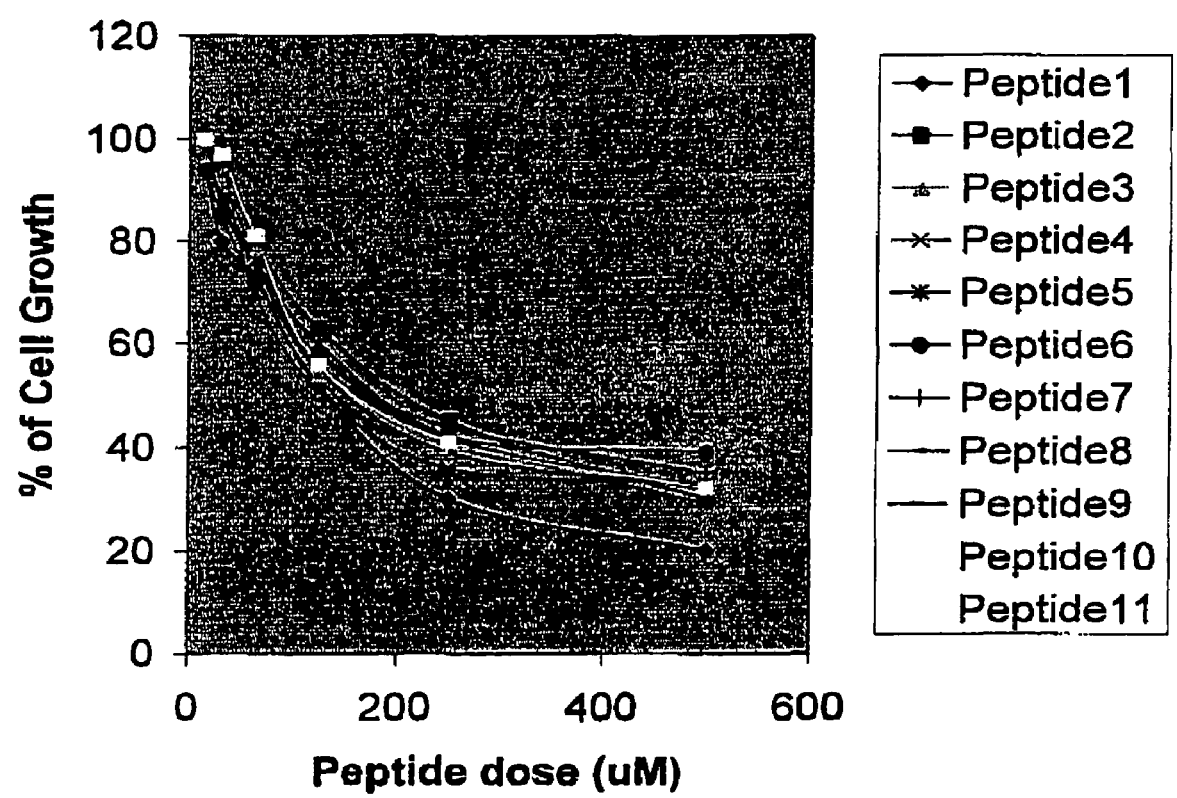
FIG. 3 A: Effect of peptides on the proliferation of CaSki cells
Figure 3B:
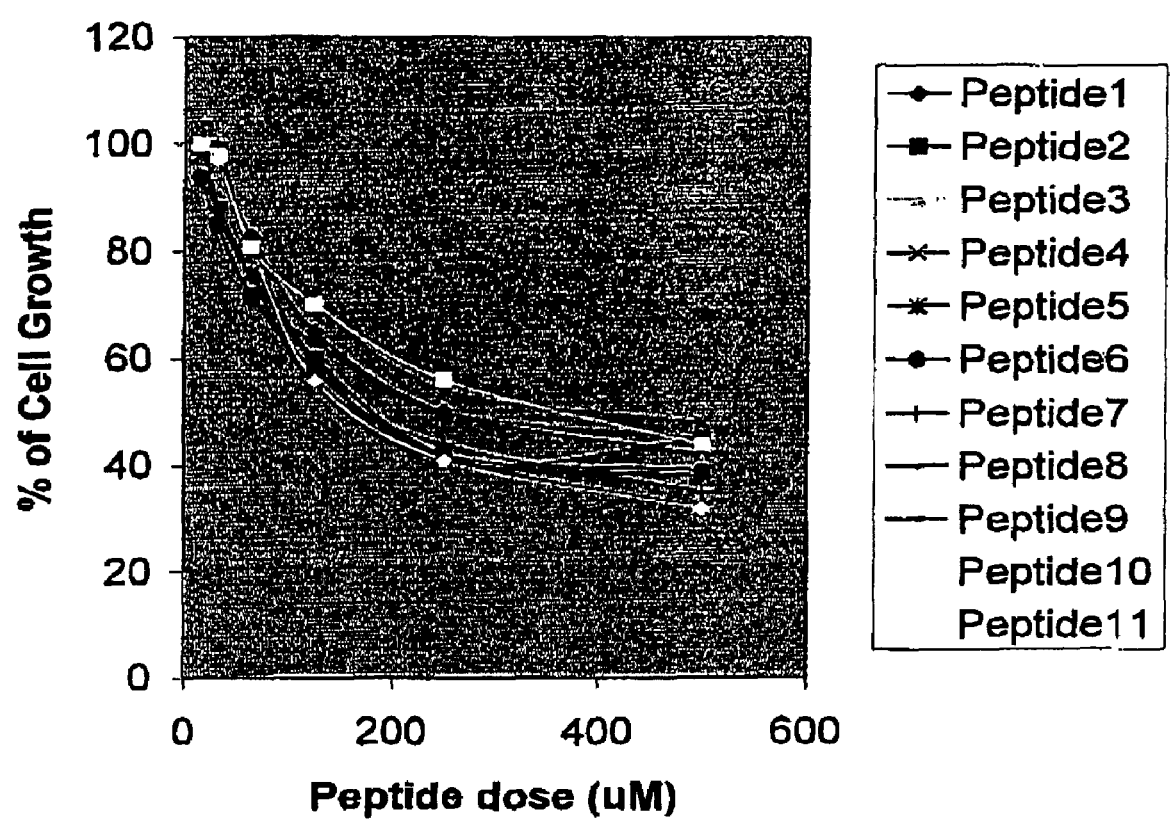
Figure 4:
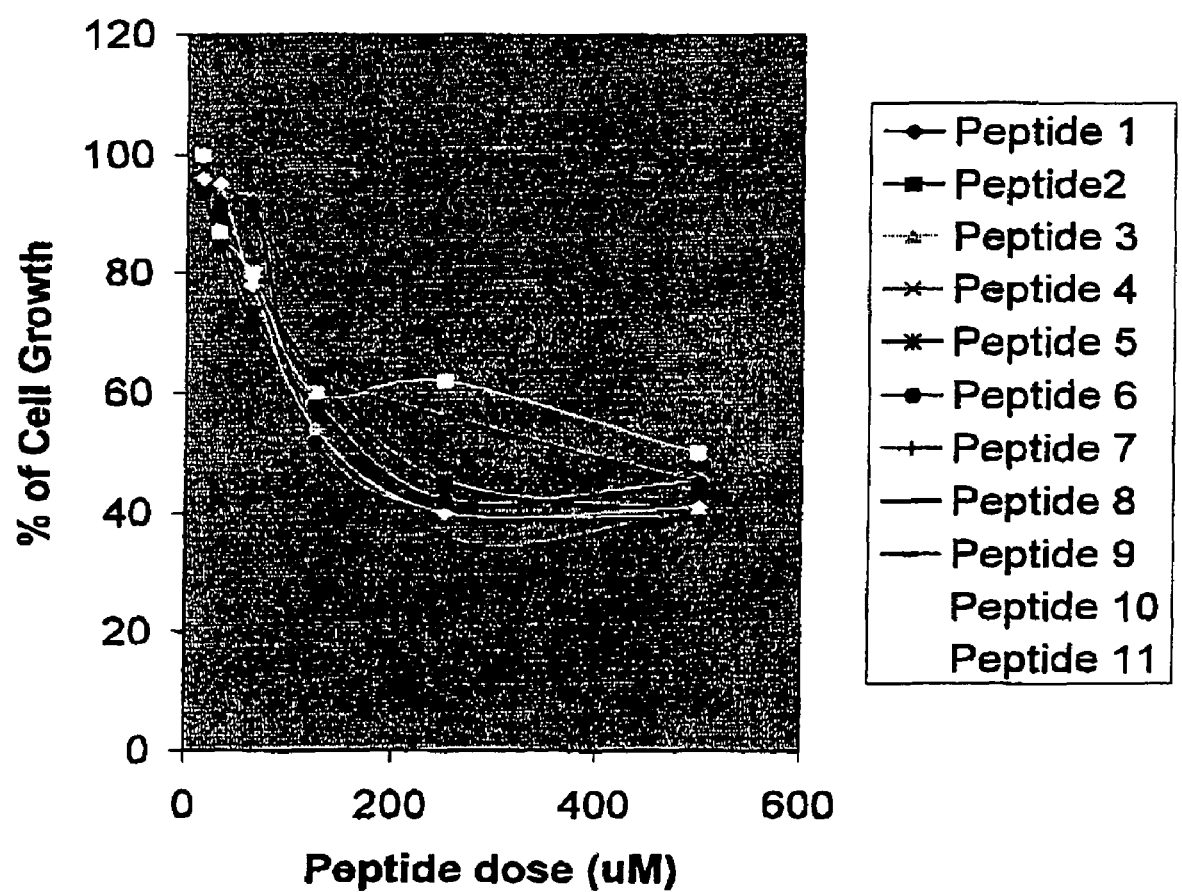
FIG. 4: Effect of peptides on the proliferation of Lung tumor cells
Figure 5:
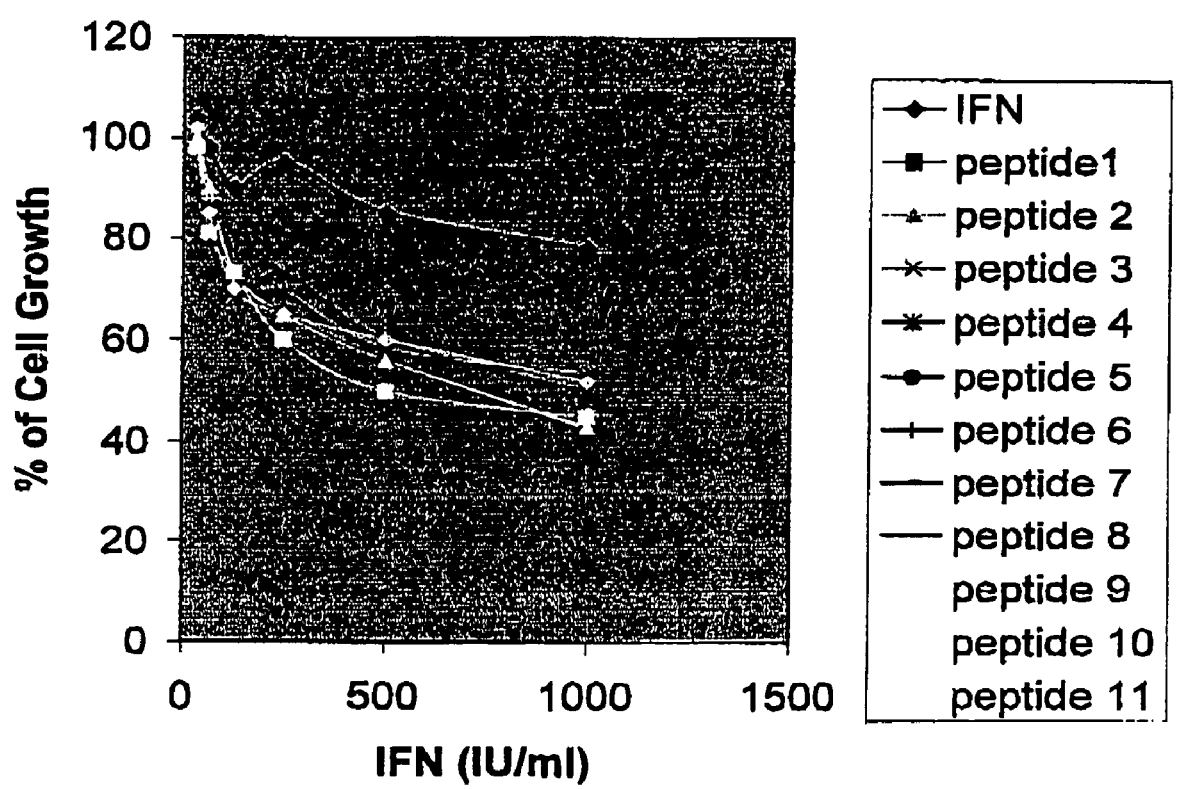
FIG. 5: Effect of peptides on the response of HPV-16 transformed cells toward IFN action

<210> SEQ ID NO 1
<211> LENGTH: 11
<212> TYPE: PRT
<213> ORGANISM: artificial sequence
<220> FEATURE:
<223> OTHER INFORMATION: synthetic peptide

<400> SEQUENCE: 1

Cys Ser Val Arg Gln Gly Pro Val Gln Lys Cys
1               5                   10

<210> SEQ ID NO 2
<211> LENGTH: 11
<212> TYPE: PRT
<213> ORGANISM: artificial sequence
<220> FEATURE:
<223> OTHER INFORMATION: synthetic peptide

<400> SEQUENCE: 2

Cys Ser Ser Cys Gln Asn Ser Pro Ala Leu Cys
1               5                   10

<210> SEQ ID NO 3
<211> LENGTH: 11
<212> TYPE: PRT
<213> ORGANISM: artificial sequence
<220> FEATURE:
<223> OTHER INFORMATION: synthetic peptide

<400> SEQUENCE: 3

Cys Gln Ile Pro Gln Arg Thr Ala Thr Arg Cys
1               5                   10

<210> SEQ ID NO 4
<211> LENGTH: 11
<212> TYPE: PRT
<213> ORGANISM: artificial sequence
<220> FEATURE:
<223> OTHER INFORMATION: synthetic peptide

<400> SEQUENCE: 4

Cys Ala Lys Gln Arg Thr Asp Pro Gly Tyr Cys
1               5                   10

<210> SEQ ID NO 5
<211> LENGTH: 11
<212> TYPE: PRT
<213> ORGANISM: artificial sequence
<220> FEATURE:
<223> OTHER INFORMATION: synthetic peptide

<400> SEQUENCE: 5

Cys Trp Met Ser Pro Arg His Leu Gly Thr Cys
1               5                   10

<210> SEQ ID NO 6
<211> LENGTH: 11
<212> TYPE: PRT
<213> ORGANISM: artificial sequence
<220> FEATURE:
<223> OTHER INFORMATION: synthetic peptide

<400> SEQUENCE: 6

Cys Arg Asn Cys Thr Val Ile Gln Phe Ser Cys
1               5                   10

<210> SEQ ID NO 7
<211> LENGTH: 11
<212> TYPE: PRT
<213> ORGANISM: artificial sequence
<220> FEATURE:
<223> OTHER INFORMATION: synthetic peptide

<400> SEQUENCE: 7

Cys His Tyr Ile Ala Gly Thr Val Gln Gly Cys
1               5                   10

<210> SEQ ID NO 8
<211> LENGTH: 11
<212> TYPE: PRT
<213> ORGANISM: artificial sequence
<220> FEATURE:
<223> OTHER INFORMATION: synthetic peptide

<400> SEQUENCE: 8

Cys Pro Leu Val Ser Leu Arg Asp His Ser Cys
1               5                   10

<210> SEQ ID NO 9
<211> LENGTH: 11
<212> TYPE: PRT
<213> ORGANISM: artificial sequence
<220> FEATURE:
<223> OTHER INFORMATION: synthetic peptide

<400> SEQUENCE: 9

Cys Lys Gln Ser Tyr Leu His His Leu Leu Cys
1               5                   10

<210> SEQ ID NO 10
<211> LENGTH: 11
<212> TYPE: PRT
<213> ORGANISM: artificial sequence
<220> FEATURE:
<223> OTHER INFORMATION: synthetic peptide

<400> SEQUENCE: 10

Cys Phe Gln Pro Leu Thr Pro Leu Cys Arg Cys
1               5                   10

<210> SEQ ID NO 11
<211> LENGTH: 11
<212> TYPE: PRT
<213> ORGANISM: artificial sequence
<220> FEATURE:
<223> OTHER INFORMATION: synthetic peptide

<400> SEQUENCE: 11

Cys Gln Ser Tyr His Glu Leu Leu Leu Gln Cys
1               5                   10

<210> SEQ ID NO 12
<211> LENGTH: 10
<212> TYPE: PRT
<213> ORGANISM: artificial sequence
<220> FEATURE:
<223> OTHER INFORMATION: synthetic peptide

<400> SEQUENCE: 12

Arg Arg Arg Glu Glu Glu Thr Glu Glu Glu

-continued

```
                1               5                    10

<210> SEQ ID NO 13
<211> LENGTH: 14
<212> TYPE: PRT
<213> ORGANISM: Human immunodeficiency virus type 1

<400> SEQUENCE: 13

Gly Arg Lys Lys Arg Arg Gln Arg Arg Pro Pro Gln Cys
1               5                    10

<210> SEQ ID NO 14
<211> LENGTH: 7
<212> TYPE: PRT
<213> ORGANISM: Simian virus

<400> SEQUENCE: 14

Lys Lys Lys Arg Lys Val Glu
1               5
```